(12) United States Patent
Howard et al.

(10) Patent No.: US 11,353,443 B2
(45) Date of Patent: Jun. 7, 2022

(54) ENHANCED RECOVERY RESPONSE PREDICTION

(71) Applicant: CONOCOPHILLIPS COMPANY, Houston, TX (US)

(72) Inventors: James J. Howard, Tulsa, OK (US); Gary Lovell, Wailuku, HI (US)

(73) Assignee: ConocoPhillips Company, Houston, TX (US)

(*) Notice: Subject to any disclaimer, the term of this patent is extended or adjusted under 35 U.S.C. 154(b) by 778 days.

(21) Appl. No.: 15/210,333

(22) Filed: Jul. 14, 2016

(65) Prior Publication Data
US 2017/0017011 A1    Jan. 19, 2017

Related U.S. Application Data

(60) Provisional application No. 62/192,140, filed on Jul. 14, 2015.

(51) Int. Cl.
*G01N 15/08* (2006.01)
*G01N 33/24* (2006.01)

(52) U.S. Cl.
CPC ......... *G01N 33/241* (2013.01); *G01N 15/088* (2013.01); *G01N 2015/0846* (2013.01)

(58) Field of Classification Search
CPC ............... G01N 15/088; G01N 33/241; G01N 2015/0846
See application file for complete search history.

(56) References Cited

U.S. PATENT DOCUMENTS

| | | | |
|---|---|---|---|
| 2011/0181701 A1* | 7/2011 | Varslot | G06T 7/30 348/46 |
| 2012/0143579 A1 | 6/2012 | Collins et al. | |
| 2012/0241149 A1 | 9/2012 | Chen et al. | |
| 2012/0310614 A1 | 12/2012 | Beattie et al. | |
| 2014/0117231 A1 | 5/2014 | Owen et al. | |
| 2014/0345862 A1 | 11/2014 | Jerauld et al. | |
| 2015/0122992 A1* | 5/2015 | Owen | G01N 23/225 250/307 |
| 2016/0063150 A1* | 3/2016 | Safonov | E21B 43/16 703/10 |
| 2016/0077023 A1* | 3/2016 | Alshehri | G01N 23/046 378/20 |
| 2016/0177686 A1* | 6/2016 | Carvajal | E21B 43/12 700/282 |

(Continued)

OTHER PUBLICATIONS

Howard et al., "Mineral Distribution in Reservoir Rocks and Its Impact on Enhanced Oil Recovery", pp. 1-6.*

(Continued)

*Primary Examiner* — John E Breene
*Assistant Examiner* — Eyob Hagos
(74) *Attorney, Agent, or Firm* — Boulware & Valoir; Tamsen Valoir (57) ABSTRACT

Methods of combining mineral composition and laboratory test results for reservoir rock samples to predict future responses to secondary and tertiary oil recovery treatments are disclosed. Particular, SEM and EDS will be combined to produce a mineral map, including mineral distribution around the rock's pore space, for comparison with laboratory data to predict and/or interpret how certain mineral distributions will respond to various fluid-rock interactions.

5 Claims, 5 Drawing Sheets

(56) References Cited

U.S. PATENT DOCUMENTS

2016/0313267 A1* 10/2016 Kwak .................... G01N 11/00

OTHER PUBLICATIONS

Howard et al., "Mineral Distribution in Reservoir Rocks and Its Impact on Enhanced Oil Recovery", pp. 1-6, (Year: 2011).*
Ubani, et. al., "Advances in Coring and Core Analysis for Reservoir Formation Evaluation", Petroleum & Coal, 54(1) 42-51, 2012.
Lemmens H. et al., From SEM Maps and EDS Maps to Numbers in Unconventional Reservoirs, SPE-168789 (2013).
International Search Report from related application, App. No. PCT/US2016/042282, dated Feb. 8, 2017.

* cited by examiner

ENHANCED RECOVERY RESPONSE PREDICTION

PRIOR RELATED APPLICATIONS

This application is a non-provisional application which claims benefit under 35 USC § 119(e) to U.S. Provisional Application Ser. No. 62/192,140 filed Jul. 14, 2015, entitled "ENHANCED OIL RECOVERY RESPONSE PREDICTION," which is incorporated herein in its entirety.

FIELD OF THE DISCLOSURE

The disclosed methods relate generally to the fields of petrophysical property evaluation and fluid analysis of subsurface rock formations.

BACKGROUND OF THE DISCLOSURE

A reservoir is a rock formation with substantially uniform rock mineral properties and spatial distribution of permeability such that the rock formation has the capability to store fluids, and has the capability for fluids to be moved therethrough by application of suitable pressure variations. Porosity, permeability, mineralogy and lithotype are key parameters when characterizing hydrocarbon-containing reservoirs. The interaction of reservoir fluids (e.g. water, oil and gas) with the pore walls of the reservoir rock is largely responsible for the flow of these fluids and their ultimate recovery from the rock. The application of various microscopy techniques offers scientists and engineers a way to gain a better understanding of the materials and key parameters that define the pore geometry.

Traditionally, there were only limited ways to analyze the pore geometry of reservoir rock samples, one of them being the use of the scanning electron microscope (SEM). A scanning electron microscope is a type of electron microscope that produces images of a sample by scanning it with a focused beam of electrons. The electrons interact with atoms in the sample, producing various signals that can be detected and that contain information about the sample's surface topography and composition. The electron beam is generally scanned in a raster scan pattern, and the beam's position is combined with the detected signal to produce an image. Although originally performed in a high vacuum, currently, specimens can be observed in high vacuum, in low vacuum, in wet conditions (in environmental SEM), and at a wide range of cryogenic or elevated temperatures.

The application of a high-energy electron beam with a material's surface results in a number of interactions that produce different types of released electromagnetic radiation and electrons that can be detected by a variety of sensors in the electron microscope. One type of detected energy is associated with secondary electrons that are emitted from surface or shallow interactions of the electron beam with the material.

Another type of detected energy is associated with backscattered electrons that are emitted after elastic scattering interactions with the electron shell of atoms that respond to differences in atomic number. Detection of backscattered electrons therefore generates images that reflect atomic number or composition of the sample.

Yet another type of detected energy are characteristic X-Rays that are produced when the incident electron beam excites ground-state electrons in an atom to another state. The change in energy states results in a distinct X-Ray spectrum for each element.

The SEM image can be generated from three-dimensional (3D) surfaces such that it captures much of the topography of the sample. Another SEM image can be generated from two-dimensional (2D) planar surfaces that have the advantage of allowing measurement of any aerial property in a random plane, which can be considered equivalent to a 3D volume measurement. One example of this relationship is that measurement of the area of a particular grain or particle is equivalent to its volume in 3D.

The resolution of an SEM image depends upon the diameter of the electron beam and the size of the interaction volume between the electron beam and the sample material. Secondary electrons sense a very shallow volume of the sample and, therefore, have the greatest resolution of all the detected energies. Backscattered electrons are generated from a much larger volume due to their greater penetration depth, and therefore have less resolution. Characteristic X-Rays require higher electron beam energies, therefore larger electron beam diameters, such that they can interact with even larger volumes of the material thereby reducing their resolution to several square microns.

Energy-dispersive X-ray spectroscopy (EDS) is an analytical technique used for the elemental analysis or chemical characterization of a sample. It relies on an interaction of some source of X-ray excitation and a sample. Its characterization capabilities are due in large part to the fundamental principle that each element has a unique atomic structure allowing for a unique set of peaks on its X-ray emission spectrum.

To stimulate the emission of characteristic X-rays from a specimen, a high-energy beam of charged particles such as electrons or protons, or a beam of X-rays, is focused into the sample being studied. At rest, an atom within the sample contains ground state (or unexcited) electrons in discrete energy levels or electron shells bound to the nucleus. The incident beam may excite an electron in an inner shell, ejecting it from the shell while creating an electron hole where the electron was. An electron from an outer, higher-energy shell then fills the hole, and the difference in energy between the higher-energy shell and the lower energy shell may be released in the form of an X-ray. The number and energy of the X-rays emitted from a specimen can be measured by an energy-dispersive spectrometer. Because the energies of the X-rays are characteristic of the difference in energy between the two shells, and of the atomic structure of the element from which they were emitted, this allows the elemental composition of the specimen to be measured.

An SEM combined with energy dispersive spectral analysis (EDS) capability can be used to make the 2D scans at nominally 1 micron resolution. The EDS spectrum generates a distinct chemical signature of the elements present at that point, which in turn can provide an interpretation of the mineralogy of each sampled point, such as clay minerals, pores, organic matter, calcite, quartz, plagioclase, pyrite, titanium dioxide, and estimates of similar materials and combinations thereof. The SEM image together with EDS data can be used to identify the pores, mineralogy and organic content of the sample.

Under high magnification, it becomes evident that many apparently solid materials (including rock and bone) have a porous microstructure that permits fluid flows. Such fluid flows are often of great interest, especially in subterranean hydrocarbon reservoirs. Accordingly, significant efforts have been expended to characterize materials in terms of their flow-related properties including porosity, permeability, and the relation between the two. Scientists typically characterize materials in the laboratory by applying selected fluids with a range of pressure differentials across the sample. Such tests often require weeks and are fraught with difficulties, including requirements for high temperatures, pressures, and fluid volumes, risks of leakage and equipment failure, and imprecise initial conditions.

The mechanisms associated with many enhanced oil recovery (EOR) processes are often ascribed to interactions between the fluids and the enclosing rock matrix. These include the accepted importance of certain clay minerals in promoting enhanced oil recovery during low-salinity waterflood, the creation of formation damage by clay mineral movement in certain brines, the alteration of wettability due to mineral/crude interactions, and the influence of iron-bearing minerals on the effectiveness of acid stimulations. However, the mineralogy of the pore walls that are in contact with the fluids is seldom determined, as most studies rely on bulk mineralogy estimates by a variety of methods.

Therefore, there exists a need for methods that incorporate rock composition when characterizing fluid-rock interactions. Ideally, such a method will focus on the reservoir rock composition in the critical region of interaction instead of relying on bulk estimates. Further, such methods should reduce the time needed for characterizing rock-fluid interactions.

SUMMARY OF THE DISCLOSURE

The disclosure describes methods of predicting reservoir rock response to enhanced oil recovery techniques using mineral maps.

In more detail, standard scanning electron microscopy (SEM) images of rock samples and energy dispersive spectrum (EDS) chemical spectra are combined on an individual pixel basis using commercial software to generate a mineral map. The concept of a mineral map includes an understanding of the spatial distribution of individual mineral types within a complex arrangement, more specifically the relationship of minerals found adjacent to the void space or pores found in reservoir rocks.

The mineral composition of the reservoir rock will then be combined with results from enhanced oil recovery (EOR) laboratory test results to improve interpretation of fluid-rock interactions based on mineral composition. This results in robust and rapid methods of evaluating a laboratory rock sample's potential response to various enhanced oil recovery processes. Further, the method can enable prediction of responses for similar rock samples, thus saving the time and expense of performing additional laboratory tests.

Reservoir rocks are typically sedimentary rocks composed of several different classes of inclusions and voids. Within a single geologic formation or stratigraphic unit, rocks will typically contain the same compositional classes, though the volume fractions of each class may vary. Since rocks within a single formation typically have the same compositional classes and similar pore-scale structure, rock samples from one location have often been used to predict relationships between properties at a different location in the same formation where a sample is not available.

In the present method, the mineral composition of a sample rock, particularly the composition adjacent to or next to the void space that defines the pore and the interface between solid mineral grains, will be combined with laboratory test results to define critical zones and mineral compositions that influence the fluid-rock interactions. This can then be used to predict how a reservoir rock with similar properties will react to other enhance recovery treatments or to predict the effectiveness of such treatments in a reservoir.

Information on the distribution of different mineral phases found on the surfaces of pores can be used to develop models that predict fluid-rock interactions. Such fluid-rock interactions include but are not limited to the adsorption-desorption behavior of hydrocarbon liquids, or inorganic dissolved solids associated with the initial formation fluids or any introduced fluid, or other chemicals introduced to the formation fluids in an attempt to alter fluid-rock properties to enhance oil recovery.

In particular, high magnification images are collected on rock samples that have been or will be undergoing laboratory testing. The source of the sample, such as in the instance of a rock formation sample, is not particularly limited. For rock formation samples, for example, the sample can be sidewall cores, whole cores, drill cuttings, outcrop quarrying samples, or other sample sources that can provide suitable samples for analysis using methods according to the present disclosure.

Flat, polished surfaces of the reservoir rock samples are used for the SEM analysis. These can include petrographic thin sections of rocks used in optical microscope analysis, which can be of normal thickness (30 µm) or thicker (100 µm), if additional material is needed for other analysis such as laser ablation or other micro-analytical technique after SEM/EDS analysis.

SEM images obtained in back-scattered electron mode (BSE) are combined with chemical analyses obtained with an EDS spectrometer to identify the mineralogy of each pixel in the SEM image. EDS analysis is a method to determine the elemental composition of individual particles or grains in a SEM sample. The technique takes advantage of the generation of characteristic x-rays when the electron beam encounters a sample. The characteristic x-rays are displayed on spectrum, which provides the elemental composition of a particle. Quantities of elements can also be calculated from the spectrum.

Any SEM and EDS instrument can be used in the methods described herein. For instance, a mineral mapping procedure could employ a scanning electron microscope (SEM) equipped with energy dispersive X-ray (EDS) spectrometers and use a computer software that automates microscope operation and data acquisition for automated mineralogy. There are several commercial systems that provide all of the required features to generate 2D distributions of minerals in reservoir rocks. However, the SEM and EDS can also be purchased separately from different manufacturers. FEI, Jeol Instruments, Tescan, and Zeiss are examples of SEM manufacturers. Oxford Instruments offers an EDS for coupling with SEM, as does Bruker Instruments (Quantax EDS).

The analytical data compilation and analysis can be performed with commercial software adapted for use on the SEM. These software programs allow for unattended data acquisition, including the collection of backscatter electron images of the rock surface that emphasizes compositional differences in the reservoir rock and the collection of EDS-based characteristic X-Ray spectra at multiple points on the surface. This data acquisition often requires control of the SEM's sample stage so as to position the sample under the electron beam for the collection of EDS spectra at discrete points.

The distance between EDS sample points and the size of the sample grid, that is the number of points in two directions often referred to as the x-y coordinates, is dependent upon the resolution of the electron beam, the size of the features of interest in the reservoir rock sample, and the time allowed for data collection. Electron beam resolution often defines a lower limit on the spacing between grid points of 2-4 microns, while larger grid spacing may be sufficient to capture sufficient detail in samples with pores and mineral grains that are 10s to 100s of microns in size.

The generation of mineralogy-based maps can be acquired with software that accompanies most modern SEM systems as long it controls image collection, stage movement and EDS spectra collection. In addition, the software can have features that allow the user to interpret a mineral phase from the EDS spectrum that is collected at each grid point. In addition, the software can have features that allow the user to extract the abundance of each mineral identified in the sample or allow the user to extract spatial information from the two-dimensional mineral maps. These spatial information features include means to measure nearest neighbor properties, such as what minerals are adjacent to each other and to the void or pore space observed in the reservoir rock image. Any features that do not accompany the SEM system software can be added to the analysis by using other commercial image processing and analysis software or by writing individual code using commonly used algorithms.

In addition to mineralogy, the obtained SEM/EDS images will also provide information on distinct features such as grains, pores and fractures. Composition, size, and shape are just some of the information expected for the distinct features. Additionally, quantitative spatial information of the mineral distribution of the sample can be gleamed from the images, particularly at the interface between solid mineral grains and void space that defines pores.

Traditional rock-fluid reaction laboratory tests on the reservoir rock samples will also be performed. In some instances, data from prior laboratory tests can be combined with newly acquired SEM/EDS spectral data. In others, the laboratory testing and SEM/EDS are performed concurrently.

Physical properties of rocks depend, generally, on two factors: composition and microstructure. The use of the SEM-EDS techniques will provide information on the grains, pores or fracture, and interfaces, as well as the void spaces, and their composition. The laboratory testing will provide real data of fluid interactions with the rock. This combination of techniques will then provide information on how the fluid interacts with the grains, pores, fractures and interfaces, allowing for correlation of rock composition and interactions. This combination should not only enhance understanding of the reservoir's physical properties, but allow for prediction of how a reservoir will respond to different hydrocarbon recovery techniques.

Any combination of the below-described laboratory procedures may be used with the present method:

Special core analysis (SCAL) procedures can be performed before enhanced recovery testing. Special core analysis is distinguished from "routine or conventional core analysis" by adding more experiments, in particular including measurements of two-phase flow properties, determining relative permeability and capillary pressure. In particular, special core analysis is a procedure for conducting flow experiments on core plugs taken from a petroleum reservoir to elucidate the flow behavior of fluids in the porous media. SCAL usually involves measuring the reservoir characteristics to determine permeability, wettability and capillary pressure, and electrical characteristics to understand resistivity, formation factor and cation-exchange capacity. Petrographic studies and sieve analysis are also types of special core analysis that can be undertaken.

Rock-fluid reaction procedures can also be performed. These can include salinity-related and rate-related tests. Salinity-related tests furnish direct indication of rock-water interaction. They allow evaluation of damage induced by drilling, completion, workover, and injection fluids. Salinity-related tests include: liquid permeability; depth of damage studies; capillary pressure; water shock; and critical cation concentration procedures. Rate-related tests measure the permeability reduction due to fines migration and can be determined in laboratory tests. These tests simulate the effect of high flow rates that exist near the wellbores of both injection and production wells. Rate-related tests can include: critical velocity; clay stabilizer effectiveness; and wettability of fines.

In other embodiments, core analyses are limited to enhanced oil recovery or improved oil recovery evaluation. This includes tests to determine relative permeability; recovery versus polymer (or other additive) concentration, flow rate, and/or water composition; compatibility of reservoir injected fluids; injectivity resistance; polymer and/or additive retardation; reactions of additive and brine with reservoir rock; and/or projections of oil recovery for specific secondary or tertiary oil production methods.

Any enhanced or improved secondary or tertiary oil recovery technique can be evaluated including immiscible floods (water or gas), miscible floods (gas, solvents), chemical floods (alkaline, polymer, surfactant, foam, hybrids); and/or thermal (steam, water, solvent, hybrids) and the tests that are performed is dependent on the proposed recovery plan. Thus, thermal evaluations need not be performed on reservoir rock from a reservoir where immiscible flooding is intended.

The quantitative spatial information on mineral distribution obtained from the SEM/EDS can then be used to identify critical regions of the pore walls and improved interpretation of a wide range of responses that occur as a result of fluid-rock interactions in the core analysis. Improved interpretation can be experienced with many interactions including, but are not limited to, wettability distribution in rocks, the response of water floods of varying brine composition that include formation damage and EOR, and various petrophysical responses, such as electrical, permeability, and NMR relaxation.

Initial laboratory results show strong correlation between the distribution of various minerals around the pore space, especially clay minerals, and the effectiveness of secondary and tertiary treatments. The present method intends to improve this aspect by identifying key mineral compositions in critical regions that influence fluid-rock interactions and/or recovery.

It should be noted that results from larger scale testing, such as field-scale testing, can also be used in the present methods. Some applications require the larger scale testing and the presently described methods are not limited to a particular reservoir rock test size. In some embodiments, SEM/EDS spectral data is collected from two or more locations along a sample rock to allow for complete compositional analysis of the entire sample. In other embodiments, a plurality of sample rocks are collected from various points or locations in a given reservoir to allow for more complete analysis of the reservoir.

This summary is provided to introduce a selection of concepts that are further described below in the detailed description. This summary is not intended to identify key or essential features of the claimed subject matter, nor is it intended to be used as an aid in limiting the scope of the claimed subject matter.

As used herein, the "formation" corresponds to a subterranean body of rock that is sufficiently distinctive and continuous. The word formation is often used interchangeably with the word reservoir.

As used herein, a "reservoir" is a formation or a portion of a formation that includes sufficient permeability and porosity to hold and transmit fluids, such as hydrocarbons or water or natural gas, and the like.

The "porosity" of the reservoir is the pore space between the rock grains of the formation that may contain fluid.

The "permeability" of the reservoir is a measurement of how readily fluid flows through the reservoir.

A "core" is a sample of rock in the shape of a cylinder. Taken from the side of a drilled oil or gas well, a core is then dissected into multiple core plugs, or small cylindrical samples measuring about 1 inch in diameter and 3 inches long. These core plugs are then dried and various features measured.

As used herein, "modal mineral abundance" is a mineralogical assessment that depicts the volume percentages of minerals that comprise the rock.

As used herein, "correlation" is used to refer to a mutual or reciprocal relation between the pore wall and/or reservoir rock composition and the rock-fluid interactions.

As used herein, a "mineral map" refers to a two-dimensional representation of the distribution of various mineral phases, including the void space or porosity, in a reservoir rock.

As used herein, a "spatial profile" refers to the variations in mineralogy or composition along a linear trace that ranges from discrete mineral grains to void or pore space.

As used herein, a "critical region" is located near the interface between distinct mineral grains and void or pore space. The dimensions of this region vary according to the size of the individual grains and pores, but should be sufficiently large enough that the sub-areas of grain and pore can be readily identified such that the interface between the two is recognizable.

Buy "obtaining" a core sample herein we do not necessarily imply contemporaneous drilling or sampling procedures as existing samples can be used.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention.

The following abbreviations are used herein:

| ABBREVIATION | TERM |
| --- | --- |
| BSE | Backscattering electron |
| EDS | Energy dispersive spectrum detector |
| EOR | Enhanced Oil Recovery |
| MLA | Mineral Liberation Analyzer |

-continued

| ABBREVIATION | TERM |
| --- | --- |
| NMR | Nuclear Magnetic Resonance |
| SCAL | Special core analysis |
| SEM | Scanning electron microscope |
| Sw | water saturation |

DESCRIPTION OF EMBODIMENTS OF THE DISCLOSURE

The disclosure provides novel methods of predicting potential responses of a rock sample or reservoir to various enhanced oil recovery processes. Greater insights in the mechanisms involved in the fluid/rock interactions are also expected.

Methods of using scanning electron microscopy coupled with an energy dispersive spectrometer to determine the qualitative mineral content of a sample are well known. While modal mineral abundances are estimated by these observational methods, a quantitative measurement of the relative proportion of each mineral phase with respect to each other and the pores is missing from these approaches. Further, no method has combined the mineral content information with actual laboratory data to quantitatively interpret fluid-rock interactions for critical regions in a rock sample.

The presently disclosed method combines the spatial information of a mineral distribution of a sample, obtained from SEM and EDS analytical techniques, with laboratory or field-scale testing results to determine to determine how a specific mineralogy reacts. This can then be used to identify compositions of the critical regions of a sample's pore wall. This information can be applied to other samples having similar critical regions or mineral distribution to predict how the sample will respond to future test and to predict the effectiveness of a secondary or tertiary oil recovery treatment.

The present methods includes any of the following embodiments in any combination(s) of one or more thereof:

In one embodiment, this disclosure describes a method of predicting fluid-rock interactions for reservoir rock, comprising: a) obtaining scanning electron microscopy (SEM) image data in back-scattered electron (BSE) mode and energy dispersive spectral (EDS) data of a reservoir rock sample; b) assigning chemical mineralogy of each pixel using the EDS spectra compared to mineral standards; c) generating a mineral map by combining said SEM image data and said EDS-based mineral assignments on an individual pixel basis; d) determining a spatial profile of chemical analysis-based mineralogy of one or more pore walls in said reservoir rock sample; e) evaluating said reservoir rock sample's response to one or more enhanced oil recovery (EOR) tests, wherein said one or more EOR tests focus on interactions between a fluid and said reservoir rock sample; f) comparing said spatial profile with results from said evaluating step e) to identify the composition of one or more critical region of pore walls; and g) predicting fluid-rock interactions for reservoir rocks having the same critical region of pore walls composition as said reservoir rock sample.

In another embodiment, this disclosure describes a method of correlating mineral composition of a reservoir rock at the pore-wall interface with fluid interactions, comprising: a) obtaining SEM image data in a BSE mode and EDS spectral data of a reservoir rock sample; b) assigning chemical mineralogy of each pixel using the EDS spectra compared to mineral standards; c) generating a mineral map by combining said SEM image data and said EDS-based mineral assignments on an individual pixel basis; d) determining a spatial profile of chemical-analysis based mineralogy of one or more pore walls in said reservoir rock sample; e) evaluating said reservoir rock sample's response to an EOR test, wherein said EOR test focuses on interactions between a fluid and said reservoir rock sample; f) comparing said spatial profile with results from said evaluating step e) to identify the composition of one or more critical region of pore walls; and g) correlating said pore mineral composition to said critical region.

In another embodiment, this disclosure describes a method for forecasting an enhanced oil recovery process for a reservoir comprising: a) acquiring a reservoir rock sample from a reservoir of interest; b) obtaining SEM image data in BSE mode and EDS spectral data of said reservoir rock sample; c) generating a mineral map by combining said SEM image data and said EDS spectral data on an individual pixel basis; d) assigning a chemical mineralogy of each pixel in said mineral map; e) determining a spatial profile of chemical mineralogy of one or more pore walls in said reservoir rock sample; f) evaluating said reservoir rock sample's response to one or more EOR laboratory test on said reservoir rock sample; g) comparing said spatial profile with results from said evaluating step e) to identify the composition of one or more critical region of pore walls; and h) forecasting enhanced oil recovery for one or more regions in said reservoir of interest having the same critical region of pore walls composition as said reservoir rock sample.

In one embodiment, the EOR test can be a secondary recovery test or a tertiary recovery test.

In one embodiment, the spatial profile includes chemical mineralogy of the interface between solid mineral grains and void space that defines the pore in the pore walls.

In one embodiment, the response can be wettability distribution, formation damage, electrical conductivity, permeability, and other single or multiple fluid phase transport properties.

The inventive methods are described in additional detail next:

The objective of coring and core analysis is to reduce uncertainty in reservoir evaluation by providing data representative of the reservoir at in situ conditions. Core derived data have been integrated with other field data to minimize reservoir uncertainties that cannot be addressed by other data sources such as well logging, well testing or seismic. The quality and reliability of core data have become more important with the ever-increasing pressure to optimize field development.

A drawback of core analysis is the time needed to properly evaluate the reservoir. Attempts have been made to limit core analysis by building prediction models incorporating mineral composition data for the core. However, correlation of mineral composition to fluid-rock interactions have been limited to qualitative descriptions of pore wall mineral compositions to models predicting formation damage, wettability alteration, and geochemical reactivity during a chemical stimulation EOR process.

Thus, there is still a need for methods that reduce the core analysis needed yet provide better interpretation of reservoir responses and better predictive power.

The present methods address one or more of these needs by combining mineral composition information with real core data to identify critical regions that influence the rock's response to recovery methods and assign compositional information to these regions. This information can then be applied to subsequent samples to predict how the rock will respond to given stimuli.

In more detail, reservoir rock samples, preferably core samples, can be obtained through normal means. The cores will be cleaned and dried according to standard industry practice and routine properties such as porosity and permeability will be measured. Ubani et al. discuss many of these methods in "Advances in Coring and Core Analysis for Reservoir Formation Evaluation".

A small petrographic thin section of the sample core or rock will be removed for analysis using SEM and EDS. Typically, approximately 30 µm thick sample is needed. However, thicker samples may be necessary if destructive analytical techniques will be performed after the SEM/EDS analysis. The remaining core will then be prepared for laboratory testing.

Figure 1:
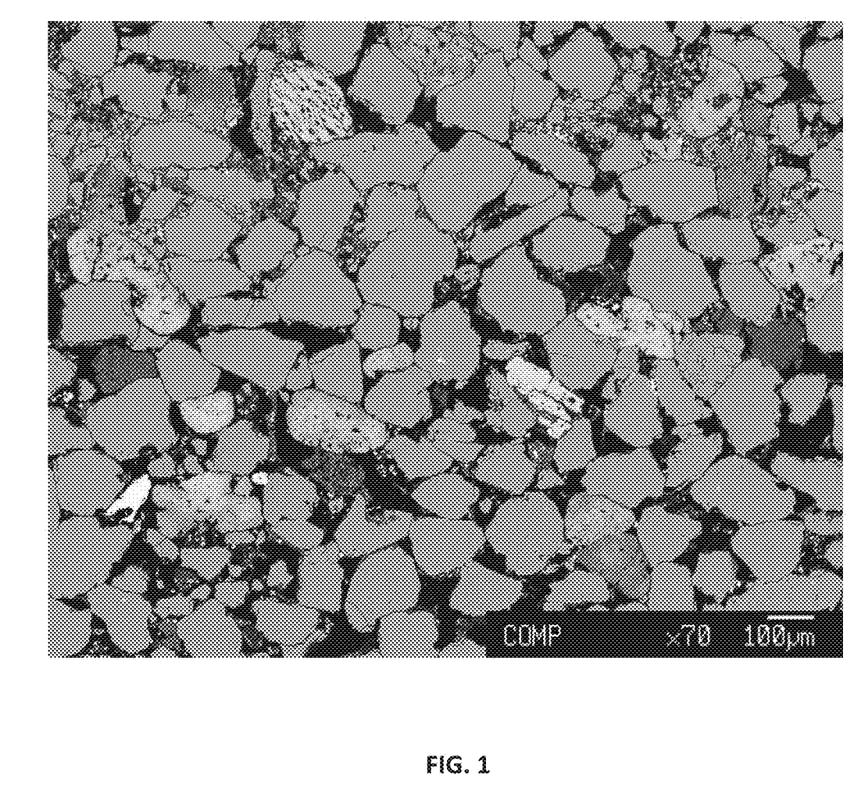
FIG. 1 depicts an exemplary SEM backscattered electron image of a rock where the variations in gray scale correspond with atomic number or grain density with the empty pores being black and mineral grains of increasing density defined by progressively lighter shades of gray.

SEM/EDS spectral data will be collected for the sample reservoir rock. The SEM data will be images, an example of which is depicted in FIG. 1, of the rock sample, including pore geometry and distributions of clay and/or other authigenic material associated with the pore system of the rock. The gray-scale on a backscattered electron image provides information on the relative density or composition of each grain or particle in the image wherein empty pores being black and mineral grains of increasing density defined by progressively lighter shades of gray.

In the case of similar compositions between two mineral phases it is difficult to separate the two based solely on gray-scale differences. For each pixel in the image, an EDS chemical spectrum will be available to provide elemental composition at that pixel. This will provide elemental composition of each individual particle or grain in the SEM image at the greatest resolution of the image as defined by the dimensions of a pixel in each image.

Figure 2:
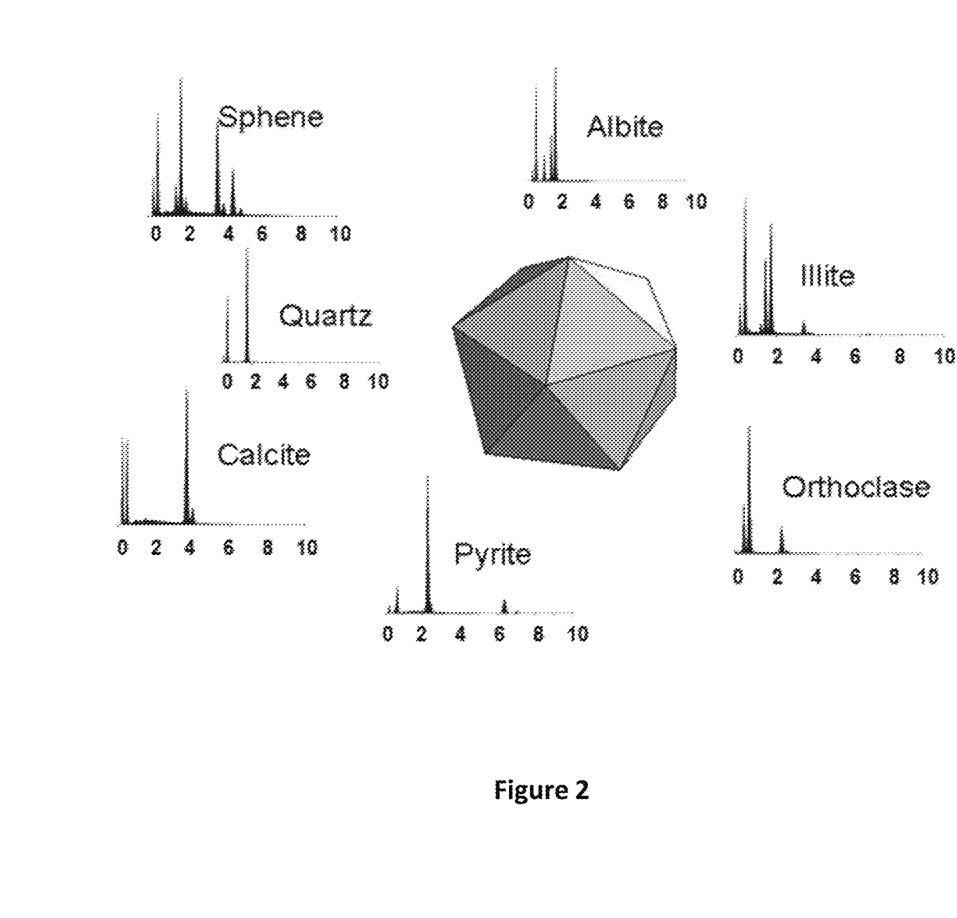
FIG. 2 depicts the process by which individual spectra of characteristic X-Rays captured at each grid point on the sample surface is interpreted as a discrete mineral phase by comparison to a set of standard spectra.

High resolution identification of mineral phases allows for the assignment of small amounts of minerals found adjacent to the pores, often referred to as the composition of the pore wall. The characteristic X-ray spectrum at each pixel is then assigned a mineral phase identification based on the "goodness-of-fit" between the spectrum and the spectra of a set of mineral standards, as shown in FIG. 2. The mineralogical analysis can be color coded, and overlaid over the SEM image, as shown in FIG. 3.

The characteristic x-rays in the EDS analysis can be used to generate a mineral map of the distribution of specific elements whose EDS spectral is known, as shown in FIG. 2. This information will be used to identify and assign the mineralogy for each pixel and to determine distinct features such as grains and pores and the like. This is in contrast to the methods of overlaying a series of element maps over the original image and assigning a mineral phase based on a simple Boolean operation of combining minerals. This latter approach works with simple ore deposits (gold vs. silver vs. platinum), but not for minerals that have similar composition. A spatial profile of chemical mineralogy, particularly on the pore walls, detailing these features will be prepared.

Figure 3:
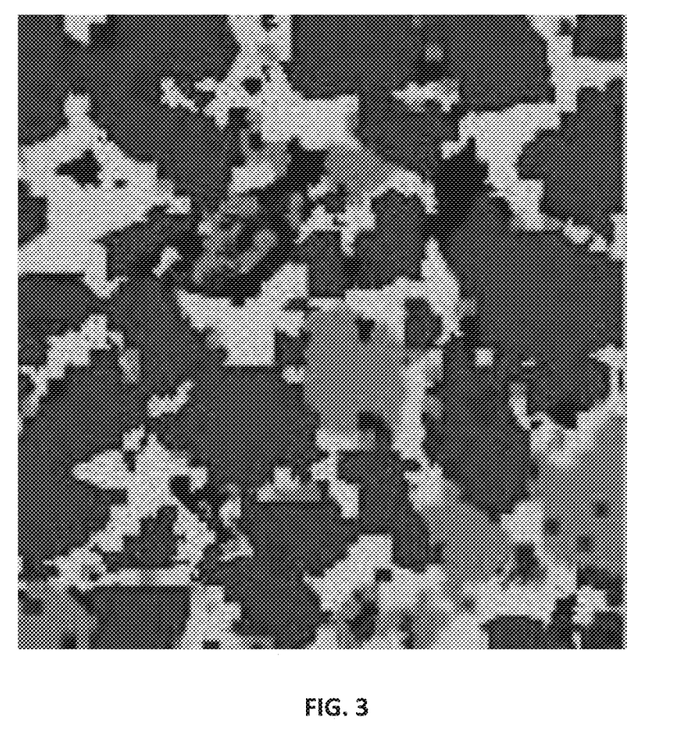
FIG. 3 depicts a mineral map where individual mineral phases identified from the characteristic X-Ray spectra are gray-scale-coded, where black represents the pore space, and various shades of gray represent different mineral phases.

Once a mineral map such as that in FIG. 3 is prepared, the distribution of mineral phases, more specifically the relative amounts of the various minerals that are adjacent to the pore space, can be compared with the responses obtained from the laboratory tests. Any correlation amongst the type of mineral phase observed on the pore wall, or the relative abundance of any particular mineral on the pore wall, or the size of the pore, and any measure of the change in fluid-rock behavior of the laboratory core test, including but not limited to relative permeability of one fluid relative to another, or changes in hydrocarbon production effectiveness as determined by changes in amount of production or rate of production, can be used to develop predictive models. In some embodiments, a larger, field size test is also performed. Results for either the lab-scale or field-scale procedures can be used with the analytical techniques data.

The techniques for performing the laboratory or field-scaled test will depend on the properties being measured and the type of oil recovery technique being studied. Below is a generalized description of steps taken to perform a core analysis and is not intended to limit the presently disclosed method to any one technique for obtaining a reservoir rock's response to various enhanced oil recovery methods.

For the e.g. laboratory test, dead crude oil (crude oil without dissolved gas) is flowed into the reservoir rock core, and the core is aged at reservoir temperature for at least six weeks to restore wettability toward reservoir conditions. The dead crude oil flowed through the core will serve to measure oil permeability at initial water saturation. The same test can be used with live crude oil (crude oil with dissolved gas) measured at temperatures and pressures approaching reservoir conditions.

Once the core is prepared, it will be flooded with a "formation brine". The formation brine core flooding will set the baseline oil recovery compared to modified brines that are used in later laboratory experiments. The composition of the formation brine is not limited and can contain other additives that are needed to establish a baseline recovery. The relative differences between flood compositions (i.e. formation brine and test solution) is expected to be representative of the order of magnitude of the impact the varying compositions would have when implemented in actual hydrocarbon recovery operations. Subsequently solutions containing chemicals and additives used in various enhance recovery methods will be flowed through the core and the core's response will be monitored for comparison with SEM/EDS mineral maps.

Responses regarding the oil recovery from the brine, formation damage, wettability alteration, and/or geochemical reactivity will be collected for use with the SEM/EDS spectral data.

The spatial profile of the rock sample, particularly around the pore, will be compared with the results from one or more laboratory tests. Correlations between the rock's responses in the tests and the spatial profile can be determined. From there, critical regions of the pore wall that influence the fluid-rock interactions can be identified and the mineral composition can be determined. These correlations can then be applied to additional reservoir samples to negate the need for separate laboratory or field scale testing. In other applications, the correlations can be used to predict how the reservoir rock sample may response to testing with similar flood compositions.

Information on the spatial distribution of minerals in a reservoir rock, especially those found adjacent to the pores can be used to predict a variety of responses associated with mineral-rock interactions during EOR processes, including but not restricted to estimating the amounts of surfactant that adsorbs to the pore wall surface, alterations in wettability due to specific adsorption of certain hydrocarbon molecules to specific mineral surfaces (for example certain asphaltenes and resins are known to adsorb preferentially to clay mineral and/or carbonate surfaces).

Correlations between mineral distribution information and the results of an enhanced oil recovery test are developed from the summary statistics of each measurement. Enhanced oil recovery tests often produce estimates of incremental oil recovery following a specific treatment, or the final saturation after said treatment, or the amounts of residual fluids after said treatment, or other estimates of the efficiency of said test. The enhanced oil recovery results for a given sample or set of samples from the same reservoir are compared to the mineral distribution results, in particular the relative percentage of each mineral of interest that is adjacent or near the pores observed in the SEM images of the sample. The correlation can be improved by using samples for the SEM-based mineral analysis that are selected directly from the core plugs used in the enhanced oil recovery or other fluid-flow SCAL tests. Often a small piece taken from one end of the core plug is used for the SEM-based mineralogy analysis.

Once completely analyzed, the correlations and results from the one or more rock samples can then be applied to a reservoir model, and reservoir performance predicted. The best EOR method can then be applied to the reservoir itself.

The present method is exemplified with respect to the enhanced oil recovery test for a waterflood described below. However, this is exemplary only, and the method can be broadly applied to any core analysis, both small and large scale. The following descriptions are intended to be illustrative only, and not unduly limit the scope of the appended claims.

Test 1

The present method was applied to suites of rock samples obtained from a sandstone reservoir under consideration for an enhanced oil recovery project. The enhance recovery method being considered was a low-salinity waterflood. This test shows how a set of sandstones from a reservoir being considered for an enhanced oil recovery project were evaluated with the spatial mineralogy process in order to gain a better understanding of the role in clay minerals in affecting ultimate recovery from that reservoir.

A set of core plugs saturated with dead oil and at initial water saturation conditions was flooded with high-salinity water under standard laboratory core flooding procedures. After the production of oil leveled off and an end point or residual oil saturation was determined, a low-salinity brine was then introduced to the core flood experiment. The amount of incremental oil that was produced in addition to the original production was measured by the change in water saturation. The incremental oil increase from the low-salinity processed ranged from 0.01 to 0.07 fractional saturation units.

Figure 4:
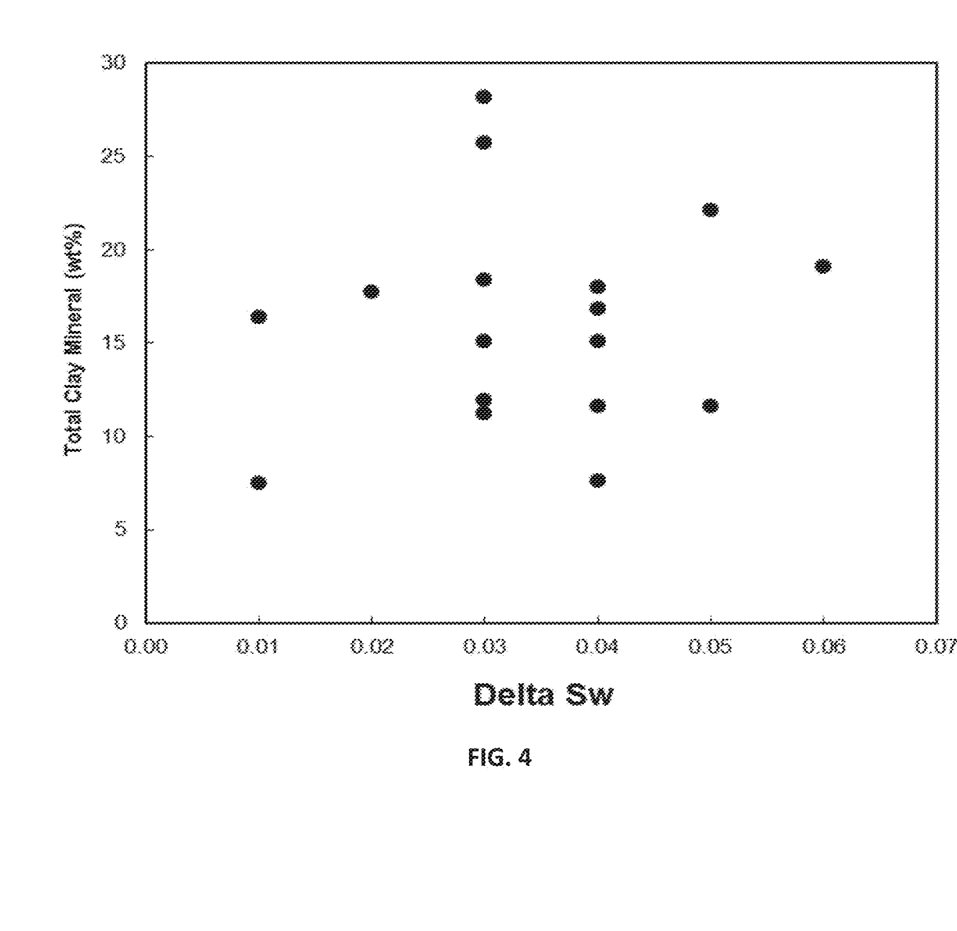
FIG. 4 depicts a correlation between the total clay mineral abundance in a set of sandstone samples as determined by traditional bulk mineralogy methods, and the improvement in oil recovery in a low-salinity waterflood as noted by changes in water saturation (Sw). The absence of a strong correlation indicates that a measure of total clay mineral content is not a good predictor of enhanced oil recovery by low-salinity waterflood methods.

Many models attempt to predict the improvement in oil recovery from low-salinity waterflood by estimating the total amount of clay minerals in the reservoir rock sample, but the results to date are equivocal. As shown in FIG. 4, the improvement in oil recovery in a low-salinity waterflood, as measured by the change in water saturation (Sw), does not correlate well with the total amount of clay minerals as measured by conventional methods.

An SEM/EDS analysis was performed and Table 1 displays the mineral concentration adjacent to a large number of pores that can be further specified by selecting a range of pore diameters that are considered as critical.

TABLE 1

Relative Mineral composition adjacent to a number of pores observed in a sandstone

| Mineral | % Adjacent to Pore |
|---|---|
| Quartz | 30.8 |
| Glauconite | 20.0 |
| Illite | 10.0 |
| Siderite | 33.0 |

The addition of spatial information on the relationship of these same clay minerals to the surface of the pore walls, from Table 1, improves the correlation that can in turn be used to predict enhanced oil recovery from a low-salinity waterflood process.

Figure 5:
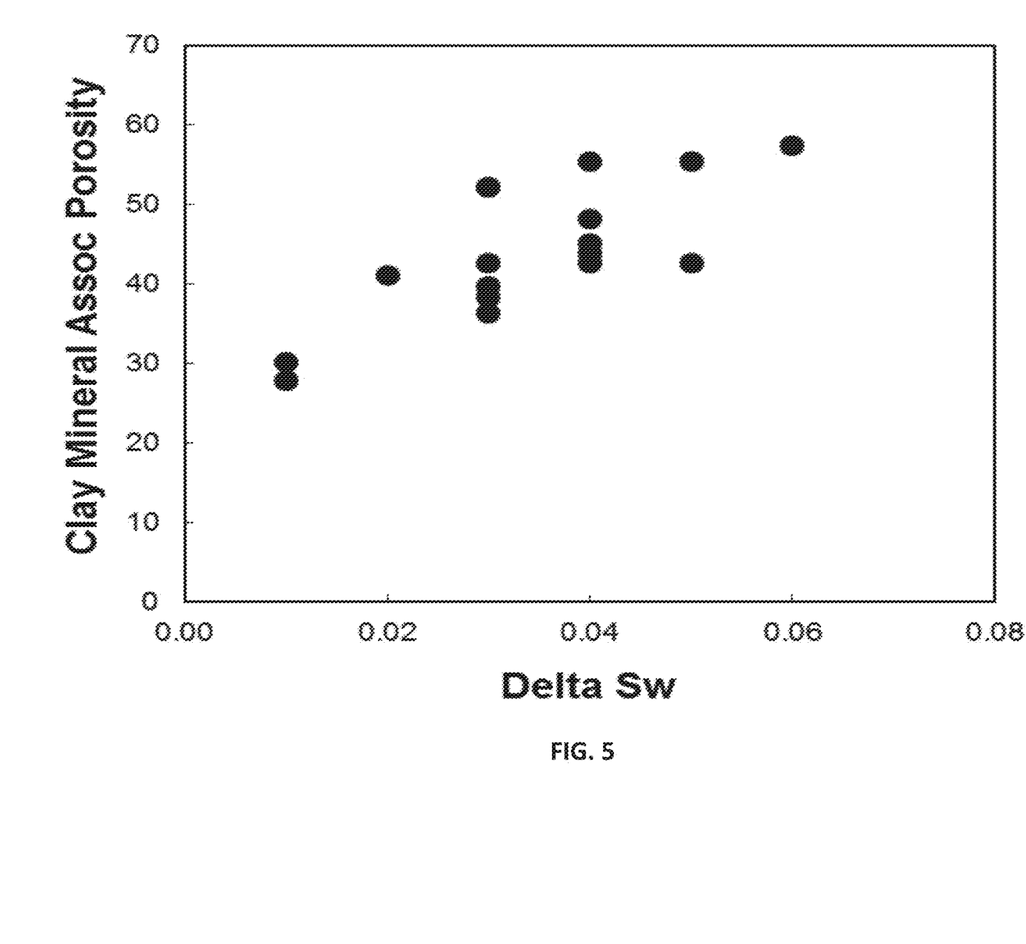
FIG. 5 depicts a correlation between the amount of clay minerals in the same set of sandstones from FIG. 4 that is adjacent to the pore space as defined by the mineral map and the amount of improved oil recovery in a low-salinity waterflood as noted by changes in water saturation (Sw). The improved correlation indicates that the addition of spatial information on the mineral composition of the pore walls yields an improved prediction tool for enhanced oil recovery by low-salinity waterflood methods.

The correlation observed in FIG. 5 relative to the absence of any definable trend in FIG. 4 illustrates how the spatial mineralogy information can be used to develop models that can predict fluid-rock interactions, including in this instance an estimate of enhanced oil recovery.

The correlation in FIG. 5 can be used to develop a single-variable linear model between the relative proportion of the pore walls associated with clay minerals and the improvement in oil recovery. These predictive models are not limited to single variables and linear trends, a multivariate, non-linear model can be constructed to predict a range of fluid-rock properties based on any number of experimental or theoretical parameters, including information on the spatial distribution of mineral phases relative to the pores.

Such models can be applied to determine an optimal recovery technique and then that best EOR actually applied to the reservoir.

The following references are incorporated by reference in their entirety.
US20140117231
Ubani, et. al., "Advances in Coring and Core Analysis for Reservoir Formation Evaluation", *Petroleum & Coal*, 54(1) 42-51, 2012. Available at: http://www.vurup.sk/sites/default/files/downloads/pc_1_2012_ubani_149_0.pdf
SPE-168789 (2013) Lemmens H. et al., From SEM Maps and EDS Maps to Numbers in Unconventional Reservoirs.
Howard, et al., "Mineral Distribution in Reservoir Oil Rocks and its Impact on Enhanced Oil Recovery", Presentation at the International Symposium of the Society of Core Analysts held in Austin, Tex., USA, Sep. 18-21, 2011.

The invention claimed is:

1. A method for improving enhanced oil recovery (EOR) from a hydrocarbon reservoir, said method comprising:
    a) obtaining one or more reservoir rock sample(s) from a reservoir of interest;
    b) obtaining scanning electron microscopy (SEM) image data in back-scattered electron (BSE) mode of said reservoir rock sample(s);
    c) obtaining energy dispersive spectral (EDS) data of said reservoir rock sample(s);
    d) generating a mineral map by combining said SEM image data and said EDS data on an individual pixel basis;
    e) assigning a chemical mineralogy of each pixel in said mineral map;
    f) determining a spatial profile of chemical mineralogy of one or more pore walls in said reservoir rock sample(s);
    g) evaluating said reservoir rock sample(s) in one or more laboratory EOR test(s);
    h) identifying a composition of one or more critical region(s) of pore walls by comparing said spatial profile with results from said evaluating step g;
    i) forecasting oil recovery for a plurality of EOR methods using a reservoir model for one or more regions in said reservoir having a same critical region of pore walls composition as said reservoir rock sample(s) from said identifying step h;
    j) selecting an optimal EOR method based on a best forecasted oil recovery from step i; and
    k) using said optimal EOR method from selecting step j to produce hydrocarbon from said reservoir.

2. The method of claim 1, wherein said one or more laboratory EOR test(s) are secondary recovery test(s).

3. The method of claim 1, wherein said one or more laboratory EOR test(s) are tertiary recovery test(s).

4. The method of claim 1, wherein said spatial profile includes chemical mineralogy of an interface between solid mineral grains and a void space that defines a pore in said pore walls.

5. The method of claim 1, wherein said one or more laboratory EOR test(s) are selected from wettability distribution, formation damage, electrical conductivity, permeability, and single or multiple fluid phase transport properties.

* * * * *